United States Patent
Löhn et al.

(10) Patent No.: US 11,981,968 B2
(45) Date of Patent: May 14, 2024

(54) CONTINUOUS METHOD FOR OBTAINING A CRYSTALLINE MONOSACCHARIDE AND DEVICE FOR CONTINUOUS CRYSTALLIZATION

(71) Applicant: BMA BRAUNSCHWEIGISCHE MASCHINENBAUANSTALT AG, Braunschweig (DE)

(72) Inventors: Mirko Löhn, Königslutter (DE); Holger Fersterra, Braunschweig (DE)

(73) Assignee: BMA BRAUNSCHWEIGISCHE MASCHINENBAUANSTALT AG, Braunschweig (DE)

( * ) Notice: Subject to any disclaimer, the term of this patent is extended or adjusted under 35 U.S.C. 154(b) by 435 days.

(21) Appl. No.: 17/293,097

(22) PCT Filed: Nov. 27, 2019

(86) PCT No.: PCT/EP2019/082685
§ 371 (c)(1),
(2) Date: May 12, 2021

(87) PCT Pub. No.: WO2020/114850
PCT Pub. Date: Jun. 11, 2020

(65) Prior Publication Data
US 2021/0404025 A1     Dec. 30, 2021

(30) Foreign Application Priority Data
Dec. 6, 2018     (DE) .......................... 102018131131.1

(51) Int. Cl.
*C13B 30/02*     (2011.01)
*C07H 1/06*     (2006.01)
(Continued)

(52) U.S. Cl.
CPC ............. *C13B 30/022* (2013.01); *C07H 1/06* (2013.01); *C07H 3/02* (2013.01); *C13B 30/002* (2013.01); *C13B 30/04* (2013.01)

(58) Field of Classification Search
CPC ..... C13B 30/022; C13B 30/002; C13B 30/04; C13B 30/02; C13B 30/08; C07H 1/06;
(Continued)

(56) References Cited

U.S. PATENT DOCUMENTS

| 2,315,699 | A | * | 4/1943 | Goepp, Jr. | ........... B01D 9/0036 568/868 |
| 2,346,517 | A | * | 4/1944 | Thompson | .............. C13B 30/02 127/15 |

(Continued)

FOREIGN PATENT DOCUMENTS

| DE | 3743015 A1 * | 8/1988 | ................ C13F 1/02 |
| DE | 4041317 A1 | 7/1991 | |

(Continued)

OTHER PUBLICATIONS

English Translation of Mantovani et al Publication DE3743015A1, published Aug. 1988. (Year: 1988).*

(Continued)

*Primary Examiner* — Joseph W Drodge
(74) *Attorney, Agent, or Firm* — Bodner & Bodner, PLLC; Gerald T. Bodner; Christian P. Bodner

(57) ABSTRACT

The invention relates to a continuous method for obtaining a crystalline monosaccharide, comprising: continuous crystallization of the monosaccharide in a main crystallizer (10), wherein crystallization by evaporation and/or crystallization by cooling is carried out continuously on a crystal suspension in the main crystallizer in order to allow crystals of the monosaccharide to grow in the crystal suspension; separa- (Continued)

Figure 1:
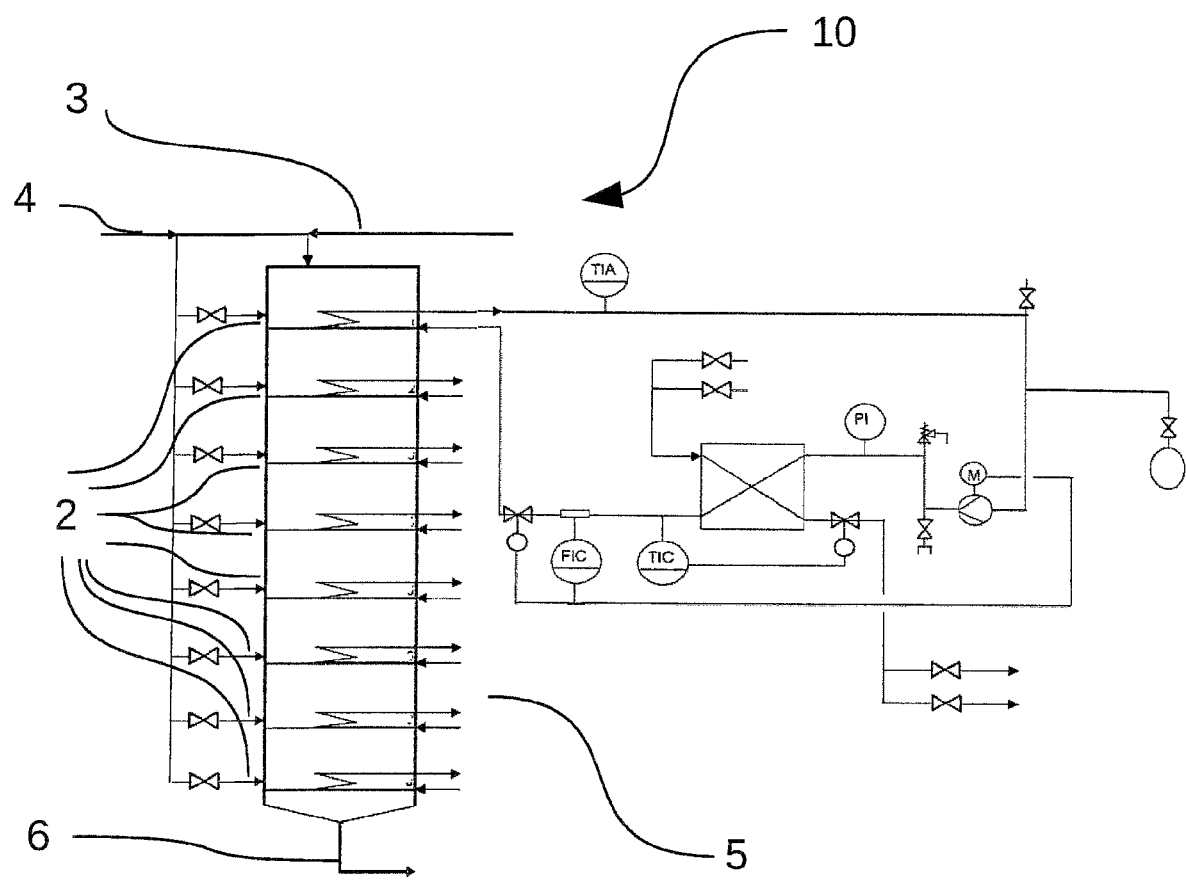

tion of crystals of the monosaccharide out of the crystal suspension to obtain crystalline monosaccharide; continuous formation of a mass of crystallization magma for the main crystallizer (10) in a cascade, wherein the cascade comprises at least one first stage (13) and a final stage (15) connected in series and each stage comprises at least one pre-crystallizer (13A, 15A), wherein, in the at least one pre-crystallizer (13A) of the first stage (13), a solution is seeded with monosaccharide by means of monosaccharide seed crystals in order to obtain a pre-crystallization magma, and a mass of crystallization magma for the downstream stage (14, 15) is formed from the pre-crystallization magma by means of crystallization by cooling and/or crystallization by evaporation, and wherein a solution containing monosaccharide and a mass of crystallization magma from the upstream stage is supplied to the at least one pre-crystallizer (15A, 15B, 15C) of the final stage (15) to obtain a pre-crystallization magma, and in the at least one pre-crystallizer (15A, 15B, 15C) of the final stage (15) a mass of crystallization magma for the main crystallizer (10) is formed from the pre-crystallisation magma by means of crystallization by cooling and/or crystallization by evaporation; the continuous supply of a solution containing the monosaccharide and a mass of crystallization magma from the at least one pre-crystallizer (15A, 15B, 15C) of the final stage (15) of the cascade to the main crystallizer (10) to provide the crystal suspension.

26 Claims, 3 Drawing Sheets

(51) Int. Cl.
    *C07H 3/02*     (2006.01)
    *C13B 30/00*     (2011.01)
    *C13B 30/04*     (2011.01)

(58) Field of Classification Search
    CPC ...... C07H 3/02; B01D 9/0022; B01D 9/0004; B01D 9/0018; B01D 9/0036; B01D 9/0059; B01D 9/0063; B01D 9/004; B01D 9/02; B01D 2009/0086; C30B 7/02; C30B 7/08; C30B 29/54
    See application file for complete search history.

(56) References Cited

U.S. PATENT DOCUMENTS

| | | | | |
|---|---|---|---|---|
| 3,879,215 A * | 4/1975 | De Villiers | .......... | B01D 9/0022 127/15 |
| 3,981,739 A | 9/1976 | Dmitrovsky et al. | .......... | 127/60 |
| 4,004,886 A * | 1/1977 | Thijssen | .............. | B01D 9/0036 62/541 |
| 5,133,807 A * | 7/1992 | De Cremoux | ........ | C13B 30/022 159/44 |
| 5,209,856 A * | 5/1993 | Cuel | ..................... | C13B 30/022 210/182 |
| 6,206,977 B1 * | 3/2001 | Nurmi | .................. | B01D 9/0013 127/15 |
| 8,735,106 B2 | 5/2014 | Hong et al. | .................... | 435/105 |
| 10,246,476 B2 | 4/2019 | Kim et al. | | |
| 10,822,666 B2 * | 11/2020 | Mahrholz | ............. | C13B 30/025 |

FOREIGN PATENT DOCUMENTS

| | | | | |
|---|---|---|---|---|
| EP | 1310504 A1 | 5/2003 | | |
| EP | 3210478 A1 | 8/2017 | | |
| KR | 1020090118465 A | 12/2009 | | |
| KR | 1020110035805 A | 4/2011 | | |
| WO | WO2016064087 A1 | 4/2016 | | |
| WO | WO2018081557 A2 * | 5/2018 | .............. | C07H 1/06 |
| WO | WO2018081557 A2 | 5/2018 | | |

OTHER PUBLICATIONS

Gnielinski, et al., "*Verdampfung, Kristallisation, Trocknung*", Springer Fachmedien Wiesbaden GmbH, 1993. Abstract and full text available at: https://www.springer.com/us/book/9783540670643dd (last accessed on Aug. 23, 2021).
Gnielinski, et al., "*Verdampfung, Kristallisation, Trocknung*", Springer Fachmedien Wiesbaden GmbH, 1993. Abstract and full text available at: https://link.springer.com/book/10.1007/978-3-642-58073-4 (last accessed on Dec. 9, 2021).
Alfons Mersmann, "*Crystallization Technology Handbook*", Marcel Dekker, Inc., 1995. Abstract available at: https://www.amazon.com/Crystallization-Technology-Handbook-Alfons-Mersmann/dp/0824792335 (last accessed on Dec. 9, 2021).
Alfons Mersmann, "*Crystallization Technology Handbook*", CRC Press, 2$^{nd}$ Edition, 2001. Abstract available at: https://www.routledge.com/Crystallization-Technology-Handbook/author/p/book/9780824745110 (last accessed on Dec. 9, 2021).
Takeshita, et al., "*Mass production of D-psicose from D-fructose by a continuous bioreactor system using immobilized D-tagatose 3-epimerase*", Journal of Bioscience and Bioengineering, vol. 90, Issue 4, pp. 453-455, Jan. 24, 2002. Abstract and full text available at: https://www.sciencedirect.com/science/article/abs/pii/S1389172301800189?via%3Dihub (last accessed on Aug. 23, 2021).
Gnielinski, et al., "*Verdampfung, Kristallisation, Trocknung*", Springer Fachmedien Wiesbaden GmbH, 1993. Abstract and full text available at: https://springer.com/us/book/9783540670643dd (last accessed on Aug. 23, 2021).
The Notification Concerning Transmittal of Copy of International Preliminary Report on Patentability (Chapter I of the Patent Cooperation Treaty), in English, dated Jun. 17, 2021, which was issued by the International Bureau of WIPO in Applicant's corresponding international PCT application having Serial No. PCT/EP2019/082685, filed on Nov. 27, 2019.
The English translation of the International Preliminary Report on Patentability (Chapter I of the Patent Cooperation Treaty), dated Jun. 8, 2021, which was issued by the International Bureau of WIPO in Applicant's corresponding international PCT application having Serial No. PCT/EP2019/082685, filed on Nov. 27, 2019.
The Written Opinion of the International Searching Authority, in English, dated Mar. 10, 2020, which was issued by the International Bureau of WIPO in Applicant's corresponding international PCT application having Serial No. PCT/EP2019/082685, filed on Nov. 27, 2019.
The International Search Report, in English, dated Mar. 10, 2020, which was issued by the International Bureau of WIPO in Applicant's corresponding international PCT application having Serial No. PCT/EP2019/082685, filed on Nov. 27, 2019.
An Office Action (in German), dated May 7, 2019, issued by the German Patent Office for Applicant's corresponding German Patent Application No. DE102018131131.1, filed Dec. 6, 2018.

\* cited by examiner

CONTINUOUS METHOD FOR OBTAINING A CRYSTALLINE MONOSACCHARIDE AND DEVICE FOR CONTINUOUS CRYSTALLIZATION

The invention relates to a continuous method for obtaining a crystalline monosaccharide and a device for obtaining a crystalline monosaccharide, in particular for performing the continuous method according to the invention.

For crystallizing saccharides, evaporation crystallizers and cooling crystallizers are employed, the construction and operating mode of which are known to the skilled person. In order to prevent spontaneous crystal formation, seed crystals or a crystallization magma containing seed crystals are added for initiating the crystallization process of a crystal-free concentrated solution containing sugar, so that crystal growth can proceed under controlled conditions in a crystallizer.

Allulose (d-psicose) is a monosaccharide from the group of ketohexoses, which has become producible in larger quantities due to the development of new methods (Takehita et al., Journal of Bioscience and Bioengineering, vol. 90, No. 4, pages 453 to 455; Korean Patent Application No. 10-2009-0118465, CJ Cheiljedang Corp. Korea).

The crystallization of allulose in an industrial scale is described in literature by a patent application or patent grant (PCT/KR2015/009449 or EP 3210478 A1, both assigned to CJ Cheiljedang Corp. Korea). It is described in the printed publication that d-psicose, after purification and concentration by applying cooling crystallization, is transferred from the liquid phase into the crystalline state, wherein the solution is cooled to 30 to 40° C. after concentration by means of a heat exchanger and permeated with seed crystals. The production of the seed crystals for initiating the allulose crystallization is not described. When the crystal growth speed decreases (when the state of equilibrium is reached), a defined quantity of the concentrated allulose solution cooled down to 30 to 40° C. is added to the crystal suspension once to twice per hour. This procedure is repeated until the crystallizer has reached its maximum working volume.

Due to the discontinuous manner of preparation, an industrial production of crystalline allulose is time-consuming and uneconomic. For other monosaccharides, as well, there is the need for enabling continuous preparation of the crystalline form or for improving existing methods and devices. A particular difficulty in the industrial preparation of crystalline sugars is to control crystal growth. On the one hand, a yield as high as possible is aspired. On the other hand, conditions enabling high yield, will not necessarily result in a method which is suitable as a large-scale, in particular continuous method. Crystal growth can be influenced by numerous factors such as, for example, the temperature of crystallization and kind of crystallization, the mixing of the crystal suspension as well as the kind of sugar. These factors thus can influence the yield, form and size of the sugar crystals. The form and the size of the crystals and the concentration thereof in the crystal suspension in turn may have an effect upon the flow behavior of the crystal suspension in a plant. If there is no success in precisely controlling the crystal growth, a large-scale and in particular continuous method is not imaginable due to the inadequate workability of the crystal suspensions. Also, with a view to further method steps, a small particle size distribution is in general aspired. A further difficulty in a continuous preparation method is to prepare a sufficiently large quantity of crystallization magma for seeding a crystallization solution.

Since, during a crystallization step, the technically achievable de-sugaring process of the solution is limited by the crystal content in a crystal suspension. A limitation of the available mass of crystallization magma is derived from the fact that the preparation methods for crystallization magma are mostly carried out discontinuously.

Therefore, the task of the present invention is to provide a continuous method for obtaining a crystalline monosaccharide and a device for obtaining a crystalline monosaccharide, in particular for performing the continuous method according to the invention.

Continuously providing a sufficiently large quantity of crystallization magma for seeding the crystallization solution is intended to be enabled by the method and the device, respectively, so that the entire method can be carried out continuously.

Further, crystal growth in the method and the device, respectively, needs to be controlled by given conditions and result in manipulable mixtures that can, e.g., be stirred and homogenized.

A further task is to enable a continuous method having high efficiency and yield in large quantities by means of the method and the device, respectively.

According to the invention, this task is solved by a method according to claim 1. With a view to the device, this task is solved by the subject matter of claim 15.

Preferably, at least one of these tasks is solved by the continuous method according to the invention for obtaining a crystalline monosaccharide, wherein the continuous method preferably comprises continuously crystallizing the monosaccharide in a main crystallizer, separating crystals of the monosaccharide out of a crystal suspension (a crystallization mixture) to obtain crystalline monosaccharide, continuously forming of a mass of crystallization magma for the main crystallizer in a cascade (of pre-crystallizers), and continuously supplying a solution containing the monosaccharide, and a mass of crystallization magma from the at least one pre-crystallizer in the final stage of the cascade to the main crystallizer in order to provide the crystal suspension. During the continuous crystallization of the monosaccharide in a main crystallizer, an evaporation crystallization and/or cooling crystallization is carried out continuously on a crystal suspension in the main crystallizer in order to allow crystals of the monosaccharide to grow in the crystal suspension. The continuous formation of a mass of crystallization magma for the main crystallizer is performed in a cascade, wherein the cascade comprises at least one first stage and a final stage connected in series, and each stage comprises at least one pre-crystallizer, wherein, in the at least one pre-crystallizer of the first stage, a solution is seeded with monosaccharide by means of monosaccharide seed crystals in order to obtain a (so-called) pre-crystallization magma, and a mass of crystallization magma for the downstream stage is formed from the pre-crystallization magma by means of cooling crystallization and/or evaporation crystallization, and wherein, in the at least one pre-crystallizer, a solution containing the monosaccharide and a mass of crystallization magma from the upstream stage is supplied to the at least one pre-crystallizer of the final stage to obtain a pre-crystallization magma, and, in the at least one pre-crystallizer of the final stage, a mass of crystallization magma for the main crystallizer is formed from the pre-crystallization magma by means of evaporation crystallization and/or cooling crystallization.

This continuous method makes it possible to obtain a crystalline efficiently and economically.

In particular, the continuous provision of crystallization magma in sufficient masses is achieved, so that the entire method can be carried out continuously.

Furthermore, crystal growth is controllable under the given conditions and results in coordinated crystal suspensions, so that the method can be carried out continuously in an industrial plant, so that the instrumentation expense is minimized. The multi-stage crystallization magma generation allows the particle size distribution to be influenced. In the subsequent continuous crystallization in the main crystallizer, the crystal size growth can thus be adjusted very precisely to the target crystal size. Furthermore, the continuous method exhibits high efficiency and yield as explained below.

The continuous crystallization of the monosaccharide in the main crystallizer is performed by cooling or alternatively by evaporating, or else by a combination of the two methods.

Evaporation crystallization can be performed at or preferably below atmospheric pressure.

The construction and operating mode of evaporation crystallizers and cooling crystallizers are known to the skilled person. Also, the performance of an evaporation crystallization and/or a cooling crystallization, in each case continuously or discontinuously, are known to the skilled person. Continuous crystallization of the monosaccharide in a main crystallizer can be carried out in case of applying cooling crystallization, for example, in a BMA OVC (vertical cooling crystallizer having oscillating cooling pipe bundles, "oscillating vertical cooling crystallizer"). Continuous crystallization of the monosaccharide in a main crystallizer can be carried out in case of applying evaporation crystallization by means of a BMA VKT (evaporation crystallization tower). As advantages, continuous crystallization results in better space-time yields, a reduction of set-up times for cleaning, filling and emptying, the achievement of higher throughput quantities at lower space requirements. In total, productivity is significantly increased, whereas a production in batches is significantly more labor-intensive.

The solutions, crystal solution, pre-crystallization magma, crystallization magma, seed suspension etc. preferably include water as a solvent in the present patent application. But other solvents, in particular alcohols and mixtures thereof with water are also imaginable.

A "solution containing the monosaccharide" describes a solution which comprises the monosaccharide and is supplied to the main crystallizer.

A "solution with monosaccharide" describes a solution which comprises the monosaccharide and is supplied to a pre-crystallizer.

In preferred embodiments, the "solution containing the monosaccharide" does not differ from the "solution with monosaccharide". In other words, the "solution with monosaccharide" is the "solution containing the monosaccharide" in preferred embodiments.

The solution with monosaccharide and the solution containing the monosaccharide may have the same integral parts and properties, i.e. be identical, or may have different integral parts and properties, i.e. be different.

The solution with monosaccharide and the mass of crystallization magma from the upstream stage may be combined in the at least one pre-crystallizer of each stage or in advance. The solution containing the monosaccharide and the mass of crystallization magma may be combined in the main crystallizer or in advance. The seeding of the solution with monosaccharide by means of monosaccharide seed crystals may be performed in the at least one pre-crystallizer of the first stage and/or in an upstream seeding device. In other words, the at least one pre-crystallizer of the first stage may comprise a seeding device.

The cooling or evaporation crystallization in one stage of the cascade may be terminated depending on the monosaccharide at any time when certain quality features of the crystallization magma (e.g. form, size, size distribution, viscosity) are reached. Since the yield (crystal mass formed with respect to the initial mass of the crystal forming substance in the solution/the solutions, or degradation of the dry substance in the liquid phase) is determined in the step of continuously crystallizing in the main crystallizer, the yields within the cascade are irrelevant for the entire method.

In order to prevent spontaneous crystal formation, solution with monosaccharide is seeded with monosaccharide seed crystals which are suspended in the solution, for initiating the crystallization process and for generating a defined crystal size in the at least one pre-crystallizer of the first stage. The addition of the monosaccharide seed crystals may be performed in a dry form or by adding in the form of a seed suspension, a so-called slurry, in which the monosaccharide seed crystals are suspended in a suspension agent. The seed suspension is prepared from crystalline monosaccharide of high purity (>99%) by crushing, preferably by grinding crystalline monosaccharide together with isopropanol or by grinding together with an oversaturated aqueous monosaccharide solution, so that the suspended particles preferably have a size of 10 to 20 μm.

For generating pre-crystallization magma or a mass of crystallization magma in the at least one pre-crystallizer of the first stage, the necessary crystal concentration (number of crystals in the quantity to be seeded) may be calculated depending on the crystal size of the seed suspension, the desired final size of the crystals, the crystal content to be achieved and the crystal form according to known calculation equations (e.g.: V. Gnielinski, A. Mersmann, F. Thurner: "*Verdampfung, Kristallisation, Trocknung*" (evaporation, crystallization, drying), Springer Fachmedien Wiesbaden GmbH 1993).

The pre-crystallization magma and the crystallization magma contain crystals of the monosaccharide.

Preferably, the pre-crystallization magma is a suspension with crystals of the monosaccharide and is formed from a solution with monosaccharide and a mass of crystallization magma or monosaccharide seed crystals.

Preferably, a crystallization magma is formed from the pre-crystallization magma in a pre-crystallizer through crystallization. The crystallization magma is preferably used for seeding a solution with monosaccharide in a pre-crystallizer and/or for seeding a solution containing the monosaccharide in the main crystallizer.

The pre-crystallization magma and the crystallization magma contain crystals of the monosaccharide.

The term "crystallizer" preferably describes a device, in particular for carrying out a crystallization process.

A pre-crystallizer preferably is a crystallizer, in particular for generating crystallization magma.

The term "main crystallizer" preferably describes a device, in which a major part of the crystalline monosaccharide is formed.

The term "dwell time" describes the hydraulic dwell time resulting from a volume of a crystallizer divided by the volume flow.

Preferred embodiments are indicated in the subclaims.

Various embodiments of the invention may be combined with one another, provided the context doesn't reveal anything else.

In a preferred embodiment, each stage comprises a single pre-crystallizer, and in the pre-crystallizer of each stage, a mass of crystallization magma is continuously formed from the pre-crystallization magma by means of evaporation crystallization.

This embodiment enables an easier configuration of the method. Evaporation crystallization can be carried out continuously, whereby a mass of crystallization magma can be formed continuously. The cascade of pre-crystallizers allows a large mass of crystallization magma to be formed.

In a further preferred embodiment, each stage comprises two to three pre-crystallizers, and in the pre-crystallizers of each stage, a mass of crystallization magma is formed from the pre-crystallization magma discontinuously by means of cooling crystallization and/or continuously by means of evaporation crystallization, wherein the mass of crystallization magma continuously supplied to the main crystallizer, when being formed discontinuously by means of cooling crystallization, is alternatingly supplied from the pre-crystallizers of the final stage.

If the crystallization magma is formed discontinuously by means of cooling crystallization in only one pre-crystallizer per stage, then a continuous supply to and also a sufficient quantity into the main crystallizer is not given. This problem can be overcome by this embodiment described above. Since each stage includes several pre-crystallizers, crystallization magma can be supplied continuously into the main crystallizer alternatingly from several pre-crystallizers, even when a discontinuous cooling crystallization in the final stage is used. In other words, the pre-crystallizers of the stages are interconnected in such a way that a continuous supply of the crystallization magma from the final stage of the cascade to the continuously working main crystallizer is guaranteed.

It should be noted in this case that not each stage needs to include the same number of pre-crystallizers. Furthermore, the pre-crystallizers of each stage can be interconnected in various ways.

Evaporation crystallization is in particular applied when the frame conditions for an evaporation crystallization of the monosaccharide are given. These are dependent on the temperature sensitivity of the solution and the solubility of the product. If solubility increases only moderately or very slightly with a rising temperature, then evaporation crystallization will preferably be applied and is then often operated under vacuum. If solubility strongly increases with a rising temperature, then the preferred crystallization method is cooling crystallization.

It is preferred in certain embodiments for the first stage to include one to two, preferably two pre-crystallizers, for the final stage to include two to four, preferably three pre-crystallizers, and for a further stage to include two to four, preferably two pre-crystallizers, wherein in the pre-crystallizers of each stage a mass of crystallization magma is formed discontinuously from the pre-crystallization magma by means of cooling crystallization, and wherein the mass of crystallization magma, which is continuously supplied to the main crystallizer, is supplied alternatingly from the pre-crystallizers of the final stage.

In a particular embodiment, in which at least one stage comprises more than one pre-crystallizer, the pre-crystallizers of the same stage each form the same mass of crystallization magma. This enables a large mass of crystallization magma to be supplied continuously into the main crystallizer alternatingly from several pre-crystallizers.

In a preferred embodiment, the mass of crystallization magma formed in a pre-crystallizer of one stage, exceeds the mass of crystallization magma formed in a pre-crystallizer of the upstream stage, by the factor of 2 to 12, preferably 4 to 7.

Thus, the mass of crystallization magma can be considerably increased with each stage so that enough crystallization magma can be ensured for continuously supplying a mass of a crystallization magma into the main crystallizer and thereby continuous crystallization of the monosaccharide can be ensured in the main crystallizer. In this case, the factor cannot be increased arbitrarily, since in the pre-crystallization magma in the pre-crystallizers, a certain concentration of supplied crystallization magma needs to be present so as to achieve an efficient and calculable crystal growth.

In a preferred embodiment, the cascade comprises between the first and the final stage one to eight, preferably one to three, most preferred one further stage or stages connected in series, wherein the further stage or the further stages in each case includes or include at least one pre-crystallizer, into which a solution with monosaccharide and a mass of crystallization magma from the upstream stage are supplied, so as to obtain pre-crystallization magma, and wherein in the at least one pre-crystallizer of each further stage, a mass of crystallization magma is formed for the downstream stage discontinuously from the pre-crystallization magma by means of cooling crystallization and/or continuously by means of evaporation crystallization.

The mass of crystallization magma supplied into the main crystallizer from the final stage of the cascade can be further increased through further stages.

Consequently, the mass of crystallization magma can be considerably increased with each additional stage, so that enough crystallization magma can be ensured for continuously supplying a mass of a crystallization magma into the main crystallizer and thus a continuous crystallization of the monosaccharide can be ensured in the main crystallizer. The preferred number of stages enables calculable crystal growth adapted to the chemical-physical properties of the monosaccharide and the desired production quantity.

In certain embodiments, the stages or the at least one pre-crystallizer are interconnected in such a way that it is possible for single further stages to be omitted.

This is in particular advantageous for being able to continuously maintain or clean the plant. Further, this is advantageous for producing smaller quantities of crystallization magma, if less crystallization magma is required for the main crystallization.

In a preferred embodiment, the monosaccharide seed crystals have an average diameter of 5 to 50 µm, preferably 10 to 20 µm. It was found out that a continuous method for obtaining crystalline monosaccharide can be carried out well in particular when the monosaccharide seed crystals have this diameter. By producing the crystallization magma in the cascade, the average particle size is increased from stage to stage. At an initial size as cited above, crystal growth in the cascade and main crystallizer is performed such that crystals having a good yield are achieved in the desired size in the main crystallizer.

In a certain preferred embodiment, a temperature gradient of the crystal suspension is adjusted over the length of the main crystallizer from 70 to 15° C., and preferably from 45 to 25° C.

In certain embodiments, cooling crystallization is continuously carried out on a crystal suspension in the main crystallizer, wherein the crystal suspension preferably is cooled down in the main crystallizer from preferably 70 to 30° C. preferably down to 35 to 15° C.

In certain similar embodiments, cooling crystallization is carried out in the main crystallizer continuously on a crystal suspension, wherein the crystal suspension is cooled down in the main crystallizer from preferably 70 to 33° C. preferably down to 32 to 15° C.

In certain embodiments, the cooling crystallization in the continuously operating main crystallizer is performed from top to bottom with a temperature gradient (temperature profile) during cooling crystallization depending on the monosaccharide. In these embodiments, the temperature of the crystal suspension in the area of supply of the solution containing the monosaccharide, and of the crystallization magma (top) preferably is from 70 to 30° C., and in the discharge area of the crystal suspension (bottom) preferably is from 35 to 15° C.

At these temperature profiles, crystal growth in a desired size and yield takes place. At the same time, the crystal suspension does not become too viscous which would aggravate further processing.

In a particularly preferred embodiment, cooling crystallization is continuously carried out on a crystal suspension in the main crystallizer, wherein the crystal suspension in the main crystallizer is cooled down preferably from 45 to 35° C., preferably down to 30 to 20° C. This embodiment is in particular preferred when it is a continuous method for obtaining crystalline allulose. At this temperature profile, crystal growth of the allulose in a desired size and yield takes place. At the same time, the crystal suspension of the allulose does not become too viscous which would aggravate further processing.

In a preferred embodiment, the dwell time of the crystal suspension in the main crystallizer is 30 to 70 hours. It was found out that crystal growth in a desired size and yield take place at this dwell time.

In a preferred embodiment, the content of each pre-crystallizer, preferably one or more solutions, suspensions, pre-crystallization magma and/or crystallization magma, is driven by a stirrer having a specific power input of 0.1 to 4 kW/m$^3$, preferably 0.5 to 2.0 kW/m$^3$. Due to the stirring process, the crystalline phase or the crystallization magma is uniformly distributed in the liquid phase or the solution with monosaccharide, whereby the material transport is promoted and the increase of the crystal mass per unit of time is elevated. Moreover, homogenization of the crystals takes place in the pre-crystallizers.

The type of stirrer, the form of stirrer and the specific energy input via the stirrer need to orient themselves to the specific viscosities in the individual stages of the cascade. At low viscosities (<0.5 Pas), preferably a diagonal blade stirrer, a paddle stirrer or a propeller stirrer is employed for suspending the crystals in the liquid phase. In the medium viscosity range (0.5 to 5.0 Pas), an intermig stirrer, a cross-arm stirrer or a blade stirrer preferably is employed. In the high viscosity range (>5.0 Pas), anchor stirrers and spiral stirrers preferably are employed.

Surprisingly, it was found that in crystallizing allulose, a focused crystal growth in the longitudinal direction could be suppressed when the specific energy input of the stirrer was increased, whereby the ratio of diameter to length of, e.g., 1:10 could be reduced to half. In case of crystals that tend to grow in length (small rods, needles), the morphology of the crystals can be influenced via the stirrer by the specific energy input. It could be observed that, if the specific energy input of the agitator was increased from, e.g., 0.5 kW/m$^3$ to, e.g., 2.0 kW/m$^3$, the growth behavior of the crystals (length growth) could be influenced so that length growth could be reduced. In contrast to saccharose, allulose has a much stronger length growth. In this respect, the stirrers have advantages which are not known from plants for saccharose. By the specific energy input of such stirrers, crystal growth is influenced in a targeted manner.

It is also imaginable for several stirrers to be used in each pre-crystallizer in order to achieve the same technical effect.

Preferably, the solution containing the monosaccharide and a mass of crystallization magma is supplied to the main crystallizer in a mass ratio of 1:5 to 1:20, preferably 1:7 to 1:11. Thus, crystalline monosaccharide can be formed efficiently in large quantities in the main crystallizer in a relatively short time and with a high yield.

Preferably for the pre-crystallization, the solution with monosaccharide has an oversaturation of 0 to 60%. In other words, the crystallization magma is provided from an upstream stage into the downstream stage and is mixed with fresh, in particular crystal-free solution with monosaccharide having an oversaturation of 0 to 60% within the metastable range. Thereby, a constantly high driving force for crystal growth is generated in each stage of the cascade.

Preferably, the dwell times in the respective stages are determined by the respectively prevailing oversaturation (state of equilibrium). The process is controlled by determining the dry substance content of the liquid phase or the crystallization magma, for example by determining the refractive index by radiometric density measurement or by microwave measurement. Alternatively, optical methods may also be employed for detecting undesired growth of new crystals and thus for process optimization.

Due to the method according to the invention, a crystallization magma having a defined number of crystals of a desired grain size and grain size distribution is developed at the end of the cascade, which can be used as crystallization magma for a controlled crystal growth in the continuously working main crystallizer.

Preferably, the solution containing the monosaccharide is oversaturated when being supplied into the main crystallizer. Thus, crystalline monosaccharide can be formed efficiently in a short time in large quantities with a high yield in the main crystallizer.

Preferably, the mass of crystallization magma, when being supplied into the main crystallizer, has a crystal content of 1 to 5% (% by weight) and/or an average particle diameter of 50 to 150 µm. Thus, crystalline monosaccharide can be formed efficiently in a short time in large quantities with high yield in the main crystallizer. At the same time, the crystals in the main crystallizer grow to a size which is favorable for further processing.

For obtaining crystalline monosaccharide, crystals of the monosaccharide having an average diameter of 200 to 400 µm and/or a purity of >99% are preferably separated. The separated crystalline monosaccharide is well suited for further processing due to the size and purity. The size and purity of the separated crystalline monosaccharide results from the proceeding according to the invention.

In certain embodiments, the pre-crystallization magma in the pre-crystallizers and/or the crystal suspension in the main crystallizer is cooled by 0.1 to 5.0 K/h. Changing the cooling rate allows the crystal growth speed to be influenced. At a cooling rate of 0.1 to 5.0 K/h, crystallization takes place in the metastable range, and the formation of fine grains by uncontrolled primary seed development or secondary seed development is avoided to the greatest possible extent. This allows homogenous crystal growth and small particle size distribution to be achieved.

In certain embodiments, the separation of crystals of the monosaccharide from the crystal suspension comprises centrifuging the crystal suspension, wherein separating may also take place continuously when centrifuging is performed alternatingly in different centrifuges.

In preferred embodiments, the method comprises a step of forming by vaporizing, from a monosaccharide-containing solution, the solution with monosaccharide preferably having an oversaturation of 0 to 60%, and/or the solution containing the monosaccharide and preferably being oversaturated.

Furthermore, the method may comprise a drying step, for example, in a fluidized bed dryer or drum dryer, which is preferably followed by product cooling, if necessary, with conditioned air.

Part of the present invention is also a crystalline monosaccharide with an average diameter of 200 to 400 µm and/or a purity of >99%.

Part of the present invention is also a crystalline monosaccharide obtained by a method according to the invention or using a device according to the invention.

As far as advantages, explanations and preferred embodiments of the crystalline monosaccharide are concerned, reference is also made to the explanations to the method and the device according to the invention, unless otherwise specified in the description.

The invention is also based on the task of proposing a device for obtaining a crystalline monosaccharide, in particular for carrying out the continuous method according to any one of claims 1 to 14. The device according to the invention comprises a main crystallizer with means for continuously carrying out an evaporation crystallization and/or a cooling crystallization on a crystal suspension for generating crystal growth of crystalline monosaccharide in the crystal suspension, means for separating crystals of the monosaccharide from the crystal suspension. The device according to the invention further comprises a cascade for continuously forming a mass of crystallization magma for the main crystallizer. The cascade comprises at least one first stage and a final stage connected in series, each having at least one pre-crystallizer, means for seeding a solution with monosaccharide by means of monosaccharide seed crystals in at least one pre-crystallizer of the first stage in order to obtain a pre-crystallization magma, and means for carrying out a cooling crystallization and/or evaporation crystallization on the pre-crystallization magma in the at least one pre-crystallizer of the first stage for forming a mass of crystallization magma for the downstream stage, and means for supplying a solution with monosaccharide and a mass of crystallization magma from the upstream stage to the at least one pre-crystallizer of the final stage to obtain a pre-crystallization magma, and means for carrying out a cooling crystallization and/or evaporation crystallization on the pre-crystallization magma in the at least one pre-crystallizer of the final stage for forming a mass of crystallization magma for the main crystallizer. The device according to the invention further comprises means for continuously supplying a solution containing the monosaccharide, and a mass of crystallization magma from the at least one pre-crystallizer of the final stage of the cascade into the main crystallizer for forming the crystal suspension.

As far as advantages, explanations and preferred embodiments are concerned, reference is also made to the explanations to the method according to the invention, which also refer to the device unless otherwise specified in the description. Furthermore, certain preferred realizations are indicated in the subclaims:

In a preferred embodiment, each stage comprises a single pre-crystallizer, and the cascade comprises means for continuously forming a mass of crystallization magma from the pre-crystallization magma in the pre-crystallizers by means of evaporation crystallization.

In a further preferred embodiment, each stage comprises two to three pre-crystallizers, and the cascade comprises means for discontinuously forming a mass of crystallization magma by means of cooling crystallization and/or for continuously forming a mass of crystallization magma by means of evaporation crystallization in the pre-crystallizers of each stage from the pre-crystallization magma. When a mass of crystallization magma is discontinuously formed by means of cooling crystallization, the cascade further comprises means for continuously supplying a mass of crystallization magma alternatingly from the pre-crystallizers of the final stage into the main crystallizer.

In certain embodiments, at least one stage of the cascade comprises more than one pre-crystallizer, and the pre-crystallizers of the same stage each include means for forming preferably equal masses of crystallization magma.

It should be noted in this case that not each stage of the cascade needs to include the same number of pre-crystallizers. Furthermore, the pre-crystallizers of each stage can be interconnected in various ways.

It is preferred in certain embodiments for the first stage to include one to two, preferably two pre-crystallizers, for the final stage to include two to four, preferably three pre-crystallizers, and for a further stage to include two to four, preferably two pre-crystallizers, and for the cascade to include means for forming discontinuously from the pre-crystallization magma in the pre-crystallizers of each stage a mass of crystallization magma by cooling crystallization, and for the cascade to include means for supplying the mass of crystallization magma continuously and alternatingly from the pre-crystallizers of the final stage to the main crystallizer.

In certain embodiments, the stages or the at least one pre-crystallizer of each stage are interconnected in such a way that it is possible for single further stages to be omitted. This is in particular advantageous for being able to continuously maintain or clean the plant. Further, this is advantageous for producing smaller quantities of crystallization magma, if less crystallization magma is required for the main crystallization.

In certain embodiments, the device comprises at least one centrifuge for separating crystals of the monosaccharide from the crystal suspension. In certain embodiments, the device comprises several centrifuges for continuously separating, wherein the centrifugation in the several centrifuges in each case preferably is performed in batches.

In certain embodiments, the device comprises a drying unit, in particular a fluidized bed dryer or drum dryer, which is followed by product cooling, if necessary, with conditioned air.

In preferred embodiments, the device comprises an evaporation station in which the solution with monosaccharide, preferably with an oversaturation of 0 to 60%, and/or the solution containing the monosaccharide, which is preferably oversaturated, is/are formed from a monosaccharide-containing solution by evaporation and preferably adjustment of a suitable evaporation rate.

Preferably, the pre-crystallizers are formed such that the mass of crystallization magma formed in the pre-crystallizers increases, starting from the first stage, by the factor of 2 to 12, preferably 4 to 7, with each stage.

Preferably, the cascade comprises between the first and the final stage one to eight, preferably one to three, most preferred one further stage or stages connected in series, wherein the further stage or the further stages in each case includes or include at least one pre-crystallizer. Furthermore, the cascade preferably includes means for supplying a solution with monosaccharide and a mass of crystallization magma from the upstream stage into the at least one pre-crystallizer of each further stage, in order to obtain pre-crystallization magma, and means for forming discontinuously from the pre-crystallization magma by means of cooling crystallization and/or continuously by means of evaporation crystallization, a mass of crystallization magma for the downstream stage in the at least one pre-crystallizer of each further stage.

The device preferably comprises means for providing monosaccharide seed crystal having an average diameter of 5 to 30 μm, preferably of 10 to 20 μm.

In preferred embodiments, the main crystallizer includes means for adjusting a temperature gradient of the crystal suspension over the length of the main crystallizer from 70 to 15° C., and preferably from 45 to 25° C.

In certain embodiments, the main crystallizer includes means for carrying out continuously a cooling crystallization on a crystal suspension in the main crystallizer, and for cooling the crystal suspension in the main crystallizer from preferably 70 to 30° C. preferably down to 35 to 15° C.

In certain embodiments, the main crystallizer includes means for carrying out continuously a cooling crystallization on a crystal suspension in the main crystallizer, and for cooling the crystal suspension in the main crystallizer from preferably 70 to 33° C. preferably down to 32 to 15° C.

In a preferred embodiment, the device is a device for obtaining crystalline allulose, and the main crystallizer includes means for carrying out continuously a cooling crystallization on a crystal suspension in the main crystallizer, and for cooling the crystal suspension in the main crystallizer from preferably 45 to 35° C. preferably down to 30 to 20° C.

Preferably, the pre-crystallizers each include a stirrer having a specific power input of 0.1 to 4 kW/m$^3$, preferably 0.5 to 2.0 kW/m$^3$.

It is also imaginable for each pre-crystallizer to include several stirrers in order to achieve the same technical effect as described above.

In preferred embodiments, the means for continuously supplying a solution containing the monosaccharide, and for continuously supplying a mass of crystallization magma into the main crystallizer are configured such that the solution containing the monosaccharide and a mass of crystallization magma is supplied to the main crystallizer in a mass ratio of 1:5 to 1:20, preferably 1:7 to 1:11.

In certain embodiments, the device comprises means for cooling the pre-crystallization magma in the pre-crystallizers and/or the crystal suspension in the main crystallizer by 0.1 to 5.0 K/h.

The monosaccharide of the method according to the invention or the device according to the invention or the monosaccharide according to the invention is in particular a monosaccharide having a melting point of 90 to 165° C. It is in particular a monosaccharide of the d configuration. Particularly preferred, it is a hexulose, a hexose, a pentose or a tetrose having a melting point of 90 to 165° C. Quite particularly preferred, the monosaccharide is a hexulose, in particular psicose (allulose), in particular d-psicose.

The invention will be explained on the basis of an exemplary embodiment with reference to the Figures.

Figure 2:
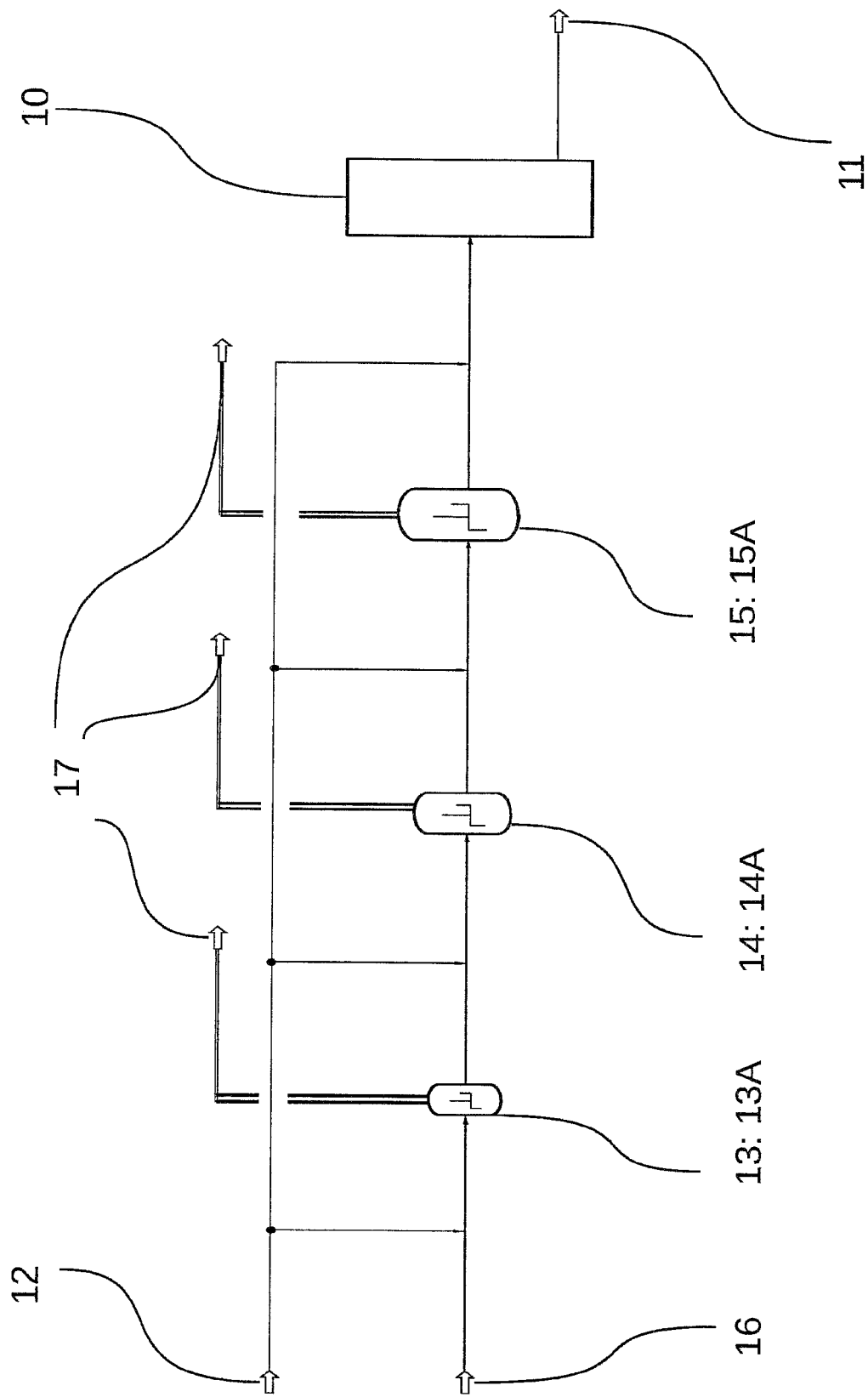
Figure 3:
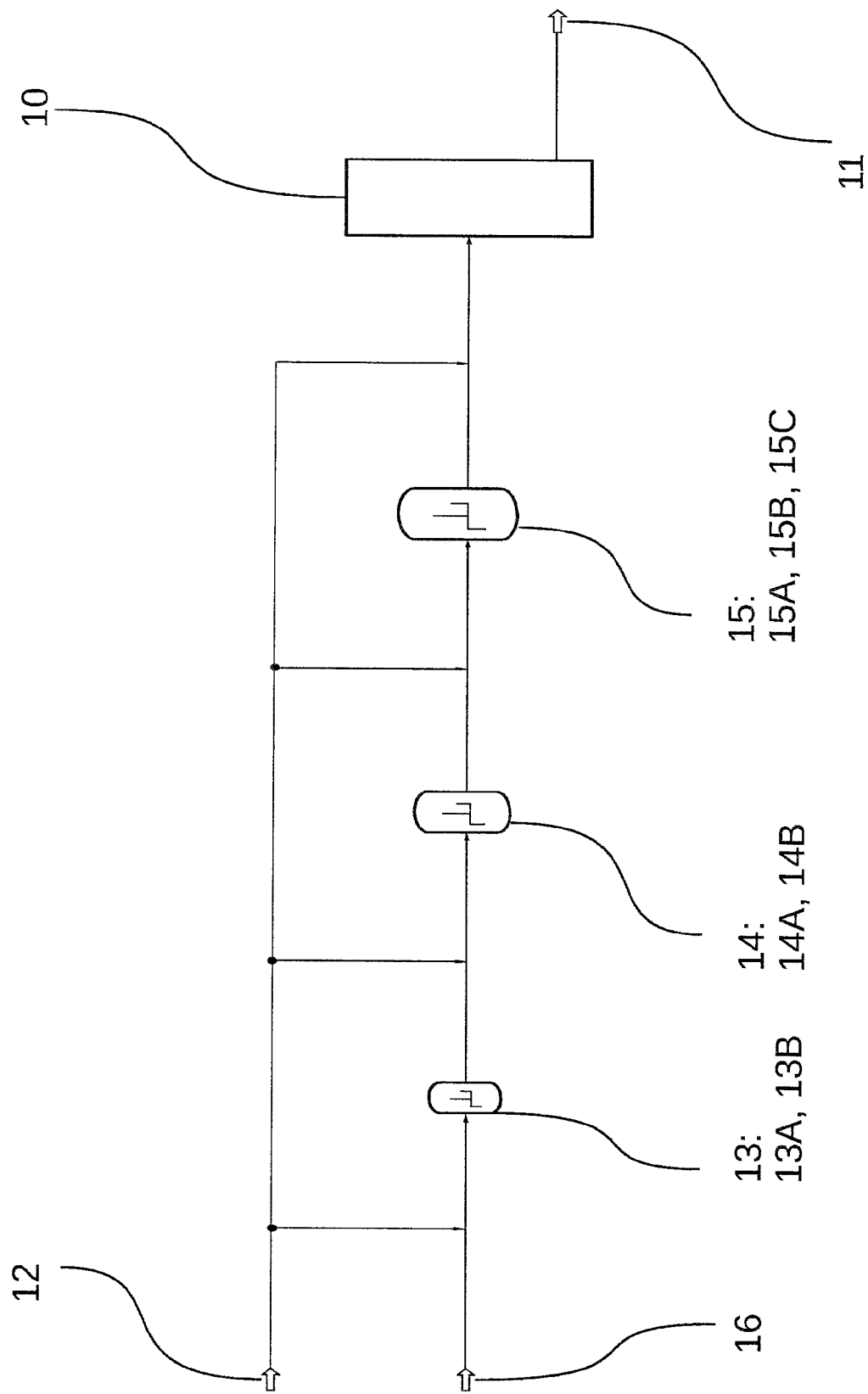

Shown are in:

FIG. 1 a main crystallizer according to a device of the present invention and in a method of the present invention;

FIG. 2 a main crystallizer and pre-crystallizers in a cascade with three stages each having a pre-crystallizer according to a device of the present invention and in a method of the present invention;

FIG. 3 a main crystallizer and pre-crystallizers in a cascade with three stages each having several pre-crystallizers according to a device of the present invention and in a method of the present invention.

FIG. 1 shows a main crystallizer 10 in a device according to the invention for carrying out the method according to the invention. In this example, the solution containing the monosaccharide and the solution with monosaccharide are identical, i.e. they contain the same integral parts in equal quantities. The solution is concentrated in an evaporation station.

The main crystallizer 10 includes injection points 2 for a solution containing the monosaccharide. The injection points 2 are distributed along the height of the main crystallizer 10 and across the circumference of the main crystallizer 10. In this example, four injection points at the same height form an injection ring. Eight of such injection rings are distributed over the height of the main crystallizer 10. The valves are clocked such that all of the injection points of one injection ring are opened or closed.

Into the top of the main crystallizer 10, a mass of crystallization magma is introduced from a line 3 of the final stage of the cascade together with a solution containing the monosaccharide from a line 4.

In this example, the main crystallizer 10 includes eight separate heat exchangers 5 in its interior for adjusting a temperature profile. The heat exchangers 5 are distributed over the height of the main crystallizer 10 and are each supplied via a water circuit for heating/cooling the crystal suspension. The flow rate and temperature of the water of the circuit are controlled so that the product temperature/the temperature profile can be influenced in a controlled manner.

From the main crystallizer 10, a discharge line 6 leads to a centrifuge station in which crystals of the monosaccharide are separated from the crystal suspension.

FIG. 2 shows an embodiment of the invention. In a main crystallizer 10, cooling crystallization is continuously carried out on a crystal suspension in order to allow crystalline monosaccharide to grow in the crystal suspension. The main crystallizer 10 is a vertical cooling crystallizer having oscillating cooling pipe bundles. Crystal suspension is continuously discharged from the main crystallizer 10, and in a centrifuge station 11, grown crystals of the monosaccharide are separated from the crystal suspension in order to obtain crystalline monosaccharide. The main crystallizer 10 is continuously supplied with a solution containing the monosaccharide, and a mass of a crystallization magma in order to provide the crystal suspension. The crystallization magma originates from a cascade for continuously forming a mass of crystallization magma.

In this example, the solution containing the monosaccharide and the solution with monosaccharide are identical, i.e. they contain the same integral parts in equal quantities. In this example, a solution containing the monosaccharide and the solution with monosaccharide, respectively, having a dry substance concentration of 82% and a temperature of 40° C. are provided in an evaporation station 12. This solution containing the monosaccharide is thus supplied to the pre-crystallizers 13A, 14A, 15A and the main crystallizer 10.

The cascade comprises three stages 13, 14, 15 connected in series, each having one pre-crystallizer 13A, 14A, 15A. In each pre-crystallizer 13A, 14A, 15A, evaporation crystallization is continuously carried out. Into the pre-crystallizer 15A of the final stage 15, a solution with monosaccharide and a mass of crystallization magma from the upstream stage 14 are supplied in order to obtain pre-crystallization magma. In the pre-crystallizer 15A of the final stage 15, a mass of crystallization magma is then formed for the main crystallizer 10 from the pre-crystallization magma by means of evaporation crystallization.

In the pre-crystallizer 13A of the first stage 13, the solution with monosaccharide is seeded with a seed suspension (the slurry) 16 with monosaccharide seed crystals of an average crystal diameter of 13 μm in order to obtain pre-crystallization magma. The seed suspension (the slurry) with monosaccharide seed crystals has a crystal content of 20% by weight and a temperature of 20° C. and is supplied at a rate of 0.30 l/h or 0.43 kg/h. A solution with monosaccharide is supplied to the pre-crystallizer 13A at a rate of 2.7 l/h. The mixture results in a pre-crystallization magma having a crystal content of 2.1% by weight. A mass of crystallization magma for the pre-crystallizer 14A of the downstream medium stage 14 is formed from the pre-crystallization magma by means of evaporation crystallization. The net volume of the pre-crystallizer 13A of the first stage 13 is 0.15 m³, exhaust vapors 17 are discharged at a temperature of 63° C. at a rate of 0.2 kg/h. The dwell time in the pre-crystallizer 13A is 43.4 h. A mass of crystallization magma is supplied to the pre-crystallizer 14A of the medium stage 14 at a rate of 2.7 l/h, a temperature of 63° C., an average crystal diameter of 30 μm, and a crystal content of 27% by weight. A solution with monosaccharide is also supplied to this pre-crystallizer 14A at a rate of 21.4 l/h.

The mixture results in a pre-crystallization magma having a crystal content of 3.2% by weight and a temperature of 42.7° C. From the pre-crystallization magma, a mass of crystallization magma for the pre-crystallizer 15A of the downstream final stage 15 is formed by means of evaporation crystallization. The net volume of the pre-crystallizer 14A of the medium stage 14 is 1.0 m³, exhaust vapors 17 are discharged at a temperature of 65° C. at a rate of 1.8 kg/h. The dwell time is 40.0 h, and a mass of crystallization magma of 21.8 l/h having a temperature of 65° C., an average crystal diameter of 60 μm, and a crystal content of 27% by weight is supplied to the pre-crystallizer 15A of the final stage 15. A solution with monosaccharide is also supplied to the pre-crystallizer 15A at a rate of 208 l/h.

The mixture results in a pre-crystallization magma having a crystal content of 2.7% by weight and a temperature of 42.5° C. From the pre-crystallization magma, a mass of crystallization magma for main crystallizer 10 is formed by means of evaporation crystallization. The net volume of the pre-crystallizer 15A of the final stage 15 is 6.0 m³, exhaust vapors 17 are discharged at a temperature of 70° C. at a rate of 14 kg/h. The dwell time is 26.7 h, and a mass of crystallization magma of 209 l/h having a temperature of 70° C., an average crystal diameter of 120 μm, and a crystal content of 22.5% by weight is supplied to the main crystallizer 10. A solution with monosaccharide, which here is identical to the solution containing the monosaccharide, is also supplied to the main crystallizer 10 at a rate of 1990 l/h.

The mixture results in a crystal suspension having a crystal content of 2.2% by weight and a temperature of 43.0° C. By means of cooling crystallization, crystalline monosaccharide is formed in the crystal suspension, but above all, crystals of crystalline monosaccharide are growing. The net volume of the main crystallizer 10 is 157.0 m³. The dwell time is 73.0 h. During this time, the crystal suspension is cooled by 0.3 K/h. The crystal suspension having the crystalline monosaccharide formed is supplied to a centrifuge station 11 at a rate of 2100 l/h having a temperature of 19° C., an average crystal diameter of 300 μm, and a crystal content of 35.3% by weight. There, crystals of the monosaccharide are separated by centrifugation, and thus, crystalline monosaccharide is obtained.

FIG. 3 shows a further embodiment of the invention. In a main crystallizer 10, cooling crystallization is continuously carried out on a crystal suspension in order to allow monosaccharide crystals to grow in the crystal suspension. The main crystallizer 10 is a vertical cooling crystallizer having oscillating cooling pipe bundles. Crystal suspension is continuously discharged from the main crystallizer 10, and in a centrifuge station 11, (grown) crystals of the monosaccharide are separated from the crystal suspension in order to obtain crystalline monosaccharide. To the main crystallizer 10, a solution containing the monosaccharide, and a mass of a crystallization magma is continuously supplied in order to obtain a crystal solution. The crystallization magma originates from a cascade for continuously forming a mass of crystallization magma.

In this example, the solution containing the monosaccharide and the solution with monosaccharide are identical, i.e. they contain the same integral parts in equal quantities. In this example, a solution containing the monosaccharide and the solution with monosaccharide, respectively, having a dry substance concentration of 82% and a temperature of 41° C., are provided in an evaporation station 12. This solution containing the monosaccharide is thus supplied to the pre-crystallizers 13A, 13B, 14A, 14B, 15A, 15B, and 15C, and the main crystallizer 10.

The cascade comprises three stages 13, 14, 15 connected in series, wherein the first stage 13 has two pre-crystallizers 13A, 13B, the medium stage 14 has two pre-crystallizers 14A, 14B, and the final stage 15 has three pre-crystallizers 15A, 15B, 15C. In each pre-crystallizer 13A, 13B, 14A, 14B, 15A, 15B and 15C, cooling crystallization is carried out discontinuously. Into the pre-crystallizers 15A, 15B and 15C of the final stage 15, a solution with monosaccharide and a mass of crystallization magma are supplied from the upstream stage 14 in order to obtain pre-crystallization magma. In the pre-crystallizers 15A, 15B and 15C of the final stage 15, a mass of crystallization magma for the main crystallizer 10 is then formed from the pre-crystallization magma by means of cooling crystallization. The cooling crystallization in the three pre-crystallizers 15A, 15B and 15C of the final stage 15 proceeds in each case discontinuously. But the cooling crystallization in the three pre-crystallizers 15A, 15B and 15C is activated such that crystallization magma can always be supplied into the main crystallizer 10 from a pre-crystallizer so that a continuous supply of crystallization magma into the main crystallizer is guaranteed. At the same time, the other pre-crystallizers can be cleaned or filled.

In the two pre-crystallizers 13A, 13B of the first stage 13, a solution with monosaccharide is seeded with a seed suspension (a slurry) 16 with monosaccharide seed crystals of an average crystal diameter of 13 μm in order to obtain pre-crystallization magma. The seed suspension (the slurry) 16 with monosaccharide seed crystals has a crystal content of 20% by weight and a temperature of 20° C. and is supplied to the pre-crystallizers 13A, 13B at a rate of 0.30 l/h or 0.43 kg/h in total. The solution with monosaccharide is supplied to the pre-crystallizers 13A, 13B at a rate of 2.6 l/h in total. The mixture results in a pre-crystallization magma having a crystal content of 2.2% by weight. A mass of crystallization magma for the two pre-crystallizers 14A, 14B of the downstream medium stage 14 is formed from the pre-crystallization magma by means of cooling crystallization. The net volume of the pre-crystallizers 13A, 13B of the first stage 13 is in each case 0.070 m³. The dwell time in the pre-crystallizers 13A, 13B is 43.3 h, the cooling rate 0.3 K/h. A mass of crystallization magma is supplied to the pre-crystallizers 14A, 14B of the medium stage 14 at a rate of 2.7 l/h in total, a temperature of 27° C., an average crystal diameter of 30 μm, and a crystal content of 27% by weight. A solution with monosaccharide is also supplied to these pre-crystallizers 14A at a rate of 20.1 l/h in total.

The mixture results in a pre-crystallization magma having a crystal content of 3.4% by weight and a temperature of 40.0° C. From the pre-crystallization magma, a mass of crystallization magma for the three pre-crystallizers 15A, 15B, 15C of the downstream final stage 15 is formed by means of cooling crystallization. The net volume of the pre-crystallizers 14A, 14B of the medium stage 14 is in each case 0.50 m³. The dwell time in the pre-crystallizers 14A, 14B of the medium stage 14 is 40.0 h, the cooling rate is 0.3 K/h. A mass of crystallization magma of 21.8 l/h in total having a temperature of 28° C., an average crystal diameter of 60 μm, and a crystal content of 27% by weight is supplied to the pre-crystallizers 15A, 15B, 15C of the final stage 15. A solution with monosaccharide is also supplied to the pre-crystallizers 15A, 15B, 15C of the final stage 15 at a rate of 197 l/h in total.

The mixture results in a pre-crystallization magma having a crystal content of 2.8% by weight and a temperature of 40.0° C. From the pre-crystallization magma, a mass of crystallization magma for main crystallizer 10 is formed by means of cooling crystallization. The net volume of the pre-crystallizers 15A, 15B, 15C of the final stage 15 is in each case 2.2 m³. The dwell time in the pre-crystallizers 15A, 15B, 15C of the final stage is 26.7 h, the cooling rate is 0.3 K/h. A mass of crystallization magma is supplied to the main crystallizer 10 at a rate of 209 l/h having a temperature of 32° C., an average crystal diameter of 120 μm, and a crystal content of 22.5% by weight. A solution with monosaccharide, which here is identical to the solution containing the monosaccharide, is also supplied to the main crystallizer 10 at a rate of 1990 l/h.

The mixture results in a crystal suspension having a crystal content of 2.2% by weight and a temperature of 40.0° C. By means of cooling crystallization, crystalline monosaccharide is formed in the crystal suspension. The net volume of the main crystallizer 10 is 157.0 m³. The dwell time is 73.0 h. During this time, the crystal suspension is cooled by 0.3 K/h. Crystal suspension having the crystalline monosaccharide formed is supplied to a centrifuge station 11 at a rate of 2100 l/h having a temperature of 19° C., an average crystal diameter of 300 μm, and a crystal content of 35.0% by weight. There, crystalline monosaccharide is separated and obtained by centrifugation.

In the examples, the purity of the crystals is >99%. The density of the solution with monosaccharide is about 1.36 kg/l. The density of the crystallization magma is about 1.44 kg/l. In the examples, each pre-crystallizer includes a stirrer having a specific power input of 0.5 to 2.0 kW/m³.

LIST OF REFERENCE NUMERALS 2 injection points
3 line for a mass of crystallization magma
4 line for a solution containing the monosaccharide
5 heat exchanger
6 discharge line to a centrifuge station
10 main crystallizer
11 centrifuge station
12 evaporation station
13 first stage of the cascade
13A, 13B pre-crystallizer(s) of the first stage
14 second, further stage of the cascade
14A, 14B pre-crystallizer(s) of the second stage
15 final stage of the cascade
15A, 15B, 15C pre-crystallizer(s) of the final stage
16 seed suspension (slurry)
17 exhaust vapors

The invention claimed is:

1. A continuous method for obtaining a crystalline monosaccharide, comprising:
    continuously crystallizing the monosaccharide in a main crystallizer (10),
    wherein, in the main crystallizer (10), an evaporation crystallization and/or cooling crystallization is carried out continuously on a crystal suspension in order to allow crystals of the monosaccharide to grow in the crystal suspension,
    separating crystals of the monosaccharide out of the crystal suspension to obtain the crystalline monosaccharide,
    continuously forming of a mass of crystallization magma in a cascade for the main crystallizer (10),
    wherein the cascade comprises at least one first stage (13) and a final stage (15) connected in series, and each stage comprises at least one pre-crystallizer (13A, 15A),
    wherein, in the at least one pre-crystallizer (13A) of the at least one first stage (13), a solution is seeded with monosaccharide by means of monosaccharide seed crystals in order to obtain a pre-crystallization magma, and a mass of crystallization magma for a downstream stage (14, 15) is formed from the pre-crystallization magma by means of cooling crystallization and/or evaporation crystallization, and
    wherein a solution with monosaccharide and a mass of crystallization magma from an upstream stage of the cascade is supplied to the at least one pre-crystallizer (15A, 15B, 15C) of the final stage (15) to obtain a pre-crystallization magma, and, in the at least one pre-crystallizer (15A, 15B, 15C) of the final stage (15), a mass of crystallization magma for the main crystallizer (10) is formed from the pre-crystallization magma by means of evaporation crystallization and/or cooling crystallization; and
    continuously supplying a solution containing the monosaccharide, and a mass of crystallization magma from the at least one pre-crystallizer (15A, 15B, 15C) of the final stage (15) of the cascade to the main crystallizer (10) in order to provide the crystal suspension.

2. The method according to claim 1, wherein each stage (13, 14, 15) of the cascade comprises a single pre-crystallizer (13A, 14A, 15A), and in the pre-crystallizer (13A, 14A, 15A) of each stage (13, 14, 15), a mass of crystallization magma is continuously formed from the pre-crystallization magma by means of evaporation crystallization.

3. The method according to claim 1, wherein each stage (13, 14, 15) of the cascade comprises two to three pre-crystallizers (13A, 13B, 14A, 14B, 15A, 15B, 15C), and in the pre-crystallizers (13A, 13B, 14A, 14B, 15A, 15B, 15C) of each stage (13, 14, 15), a mass of crystallization magma is formed from the pre-crystallization magma discontinuously by means of cooling crystallization and/or continuously by means of evaporation crystallization, when the mass of crystallization magma is being formed discontinuously by cooling crystallization, and the mass of crystallization magma continuously supplied to the main crystallizer (10) is alternatingly supplied from the pre-crystallizers (15A, 15B, 15C) of the final stage (15).

4. The method according to claim 1, wherein at least one stage (13, 14, 15) of the cascade comprises more than one pre-crystallizer, and the pre-crystallizers (13A, 13B, 14A, 14B, 15A, 15B, 15C) of a same stage (13, 14, 15) each form a same mass of crystallization magma.

5. The method according to claim 1, wherein the mass of crystallization magma formed in a pre-crystallizer (14A, 14B, 15A, 15B, 15C) of one stage (14, 15) of the cascade, exceeds the mass of crystallization magma formed in a pre-crystallizer (13A, 13B, 14A, 14B, 15A, 15B, 15C) of the respective upstream stage (13, 14), by a factor of 2 to 12.

6. The method according to claim 1, wherein the cascade comprises between the at least one first stage (13) and the final stage (15), one to eight further stages (14) connected in series, wherein at least one further stage (14) includes at least one pre-crystallizer (14A, 14B), into which a solution with monosaccharide and a mass of crystallization magma from the upstream stage (13) are supplied, so as to obtain pre-crystallization magma, and wherein in the at least one pre-crystallizer (14A, 14B) of each further stage (14), a mass of crystallization magma is formed for the downstream stage (15) discontinuously from the pre-crystallization magma by means of cooling crystallization and/or continuously by means of evaporation crystallization.

7. The method according to claim 1, wherein the monosaccharide seed crystals have an average diameter of 5 to 50 µm.

8. The method according to claim 1, wherein a temperature gradient of the crystal suspension is adjusted over a length of the main crystallizer (10) from 70 to 15° C. and/or the dwell time of the crystal suspension in the main crystallizer (10) is 30 to 70 hours.

9. The method according to claim 1, wherein the content of each pre-crystallizer (13A, 13B, 14A, 14B, 15A, 15B, 15C) of the cascade is driven by a stirrer having a specific power input of 0.1 to 4 kW/m$^3$.

10. The method according to claim 1, wherein the solution containing the monosaccharide, and a mass of crystallization magma is supplied to the main crystallizer (10) in a mass ratio of 1:5 to 1:20.

11. The method according to claim 1, wherein the solution with monosaccharide supplied to the pre-crystallizers of any stage has an oversaturation of 0 to 60% of monosaccharide, and/or the solution containing the monosaccharide, when being supplied into the main crystallizer (10), is oversaturated.

12. The method according to claim 1, wherein the mass of crystallization magma, when being supplied into the main crystallizer (10), has a crystal content of 1 to 5% (% by weight) and/or an average particle diameter of 50 to 150 µm.

13. The method according to claim 1, wherein, for obtaining crystalline monosaccharide, crystals of the monosaccharide having an average diameter of 200 to 400 µm and/or a purity of >99% are separated.

14. The method according to claim 1, wherein the pre-crystallization magma in the pre-crystallizers (13A, 13B, 14A, 14B, 15A, 15B, 15C) of the cascade and/or the crystal suspension in the main crystallizer (10) is cooled by 0.1 to 5.0 K/h.

15. The method according to claim 1, wherein the monosaccharide has a melting point of 90 to 165° C.

16. A device for obtaining a crystalline monosaccharide for carrying out the method according to claim 1, comprising:
   a main crystallizer (10) with
   an evaporation crystallizer for continuously carrying out an evaporation crystallization and/or a cooling crystallizer for carrying out a cooling crystallization on a crystal suspension for generating crystal growth of crystalline monosaccharide in the crystal suspension,
   a centrifuge station (11) for separating crystals of the monosaccharide from the crystal suspension,
   a cascade for continuously forming a mass of crystallization magma for the main crystallizer, wherein the cascade comprises:
   at least one first stage (13) and a final stage (15) connected in series, each having at least one pre-crystallizer (13A, 13B, 15A, 15B, 15C),
   a seeding device for seeding a solution with monosaccharide by means of monosaccharide seed crystals in at least one pre-crystallizer (13A, 13B) of the at least one first stage (13) in order to obtain a pre-crystallization magma, and a cooling crystallizer for carrying out a cooling crystallization and/or an evaporation crystallizer for carrying out an evaporation crystallization on the pre-crystallization magma in the at least one pre-crystallizer (13A, 13B) of the at least one first stage (13) for forming a mass of crystallization magma for a downstream stage,
   an evaporation station (12) for supplying a solution with monosaccharide and a mass of crystallization magma from an upstream stage of the cascade to the at least one pre-crystallizer (15A, 15B, 15C) of the final stage (15) to obtain a pre-crystallization magma, and a cooling crystallizer for carrying out a cooling crystallization and/or an evaporation crystallizer for carrying out an evaporation crystallization on the pre-crystallization magma in the at least one pre-crystallizer (15A, 15B, 15C) of the final stage for forming a mass of crystallization magma for the main crystallizer (10); and
   two lines (3, 4) for continuously supplying a solution containing the monosaccharide, and a mass of crystallization magma from the at least one pre-crystallizer (15A, 15B, 15C) of the final stage (15) of the cascade into the main crystallizer (10) for forming the crystal suspension.

17. The device according to claim 16, wherein each stage (13, 14, 15) of the cascade comprises a single pre-crystallizer (13A, 14A, 15A), and the cascade comprises an evaporation crystallizer for continuously forming a mass of crystallization magma from the pre-crystallization magma by means of evaporation crystallization in the pre-crystallizers (13A, 14A, 15A).

18. The device according to claim 16, wherein each stage (13, 14, 15) of the cascade comprises two to three pre-crystallizers (13A, 13B, 14A, 14B, 15A, 15B, 15C), and the cascade comprises a crystallizer for forming a mass of crystallization magma from the pre-crystallization magma discontinuously by means of cooling crystallization and/or for forming a mass of crystallization magma continuously by means of evaporation crystallization in the pre-crystallizers (13A, 136, 14A, 14B, 15A, 15B, 15C) of each stage (14, 14, 15), when the mass of crystallization magma is being formed discontinuously by means of cooling crystallization, the cascade comprises a cooling crystallizer for continuously supplying a mass of crystallization magma alternatingly from the pre-crystallizers (15A, 15B, 15C) of the final stage (15) to the main crystallizer.

19. The device according to claim 16, wherein at least one stage (13, 14, 15) of the cascade comprises more than one pre-crystallizer (13A, 13B, 14A, 14B, 15A, 15B, 15C), and the pre-crystallizers (13A, 13B, 14A, 14B, 15A, 15B, 15C) of a same stage (13, 14, 15) each include a seeding device for forming a same mass of crystallization magma.

20. The device according to claim 16, wherein the pre-crystallizers (13A, 13B, 14A, 146,15A, 15B, 15C) of the cascade are formed such that the mass of crystallization magma formed in the pre-crystallizers increases starting from a first stage (13) by the factor of 2 to 12 with each stage (14, 15).

21. The device according to claim 16, wherein the cascade comprises between the at least one first stage (13) and the final stage (15), one to eight further stages (14) connected in series, wherein the at least one further stage (14) includes at least one pre-crystallizer (14A, 14B), and the cascade includes an evaporation station (12) for supplying into the at least one pre-crystallizer (14A, 14B) of each further stage (14) a solution with monosaccharide and a mass of crystallization magma from the upstream stage (13) of the cascade, so as to obtain pre-crystallization magma, and the cascade comprises a seeding device for forming in the at least one pre-crystallizer (14A, 14B) of each further stage a mass of crystallization magma for the downstream stage discontinuously from the pre-crystallization magma by means of cooling crystallization and/or continuously by means of evaporation crystallization.

22. The device according to claim 16, wherein the device comprises a seeding device for providing monosaccharide seed crystals having an average diameter of 5 to 50 μm.

23. The device according to claim 16, wherein the main crystallizer (10) has a heat exchanger (5) for adjusting a temperature gradient of the crystal suspension over the length of the main crystallizer (10) from 70 to 15° C.

24. The device according to claim 16, wherein the pre-crystallizers (13A, 13B, 14A, 14B, 15A, 15B, 15C) of the cascade each include a stirrer having a specific power input of 0.1 to 4.0 kW/m$^3$.

25. The device according to claim 16, wherein the evaporation crystallizer for continuously supplying a solution containing the monosaccharide, and for continuously supplying a mass of crystallization magma into the main crystallizer (10) are configured such that the solution containing the monosaccharide and a mass of crystallization magma are supplied to the main crystallizer (10) in a mass ratio of 1:5 to 1:20.

26. The device according to claim 16, wherein the device comprises a heat exchanger (5) for cooling the pre-crystallization magma in the pre-crystallizers (13A, 13B, 14A, 14B, 15A, 15B, 15C) of the cascade and/or the crystal suspension in the main crystallizer (10) by 0.1 to 5.0 K/h.

* * * * *